United States Patent [19]

Mulholland et al.

[11] Patent Number: 4,703,007

[45] Date of Patent: Oct. 27, 1987

[54] SEPARATION OF VOLATILES FROM AQUEOUS SOLUTIONS BY GAS STRIPPING

[75] Inventors: D. Lindsay Mulholland, Puslinch; John D. Sheppard, Montreal, both of Canada

[73] Assignee: Ontario Research Foundation, Mississauga, Canada

[21] Appl. No.: 716,398

[22] Filed: Mar. 27, 1985

[30] Foreign Application Priority Data

Mar. 27, 1984 [GB] United Kingdom ............... 8407828

[51] Int. Cl.$^4$ ............................................. C12M 1/04
[52] U.S. Cl. ..................................... 435/161; 55/256; 55/257 HE; 435/287
[58] Field of Search .................. 55/256, 257 HE, 255; 261/77, 152; 435/287, 288

[56] References Cited

U.S. PATENT DOCUMENTS

| | | | |
|---|---|---|---|
| 3,910,826 | 10/1975 | Kataoka | 261/77 X |
| 4,337,315 | 6/1982 | Fukushima | 435/313 |
| 4,446,030 | 5/1984 | Schmidt | 261/77 X |
| 4,545,945 | 10/1985 | Prave | 261/77 X |

Primary Examiner—Alan Cohan
Attorney, Agent, or Firm—Shoemaker and Mattare, Ltd.

[57] ABSTRACT

Process and apparatus for the recovery of low concentrations of volatile components from a liquid by use of a stripping gas is disclosed. The system is particularly suited for recovery of low concentration volatile metabolites from fermentation broths.

16 Claims, 5 Drawing Figures

SEPARATION OF VOLATILES FROM AQUEOUS SOLUTIONS BY GAS STRIPPING

FIELD OF THE INVENTION

This invention relates to method and apparatus for the gaseous stripping of a volatile component from a solution.

BACKGROUND OF THE INVENTION

Gaseous stripping of volatile components from a solution using gases has been a common procedure, particularly when the volatile component or the solution to be stripped is sensitive to temperature distillation processes. For example, U.S. Pat. No. 2,718,275 discloses a degasifying apparatus where a gas such as air is forced through the solution to remove gases contained in the solution, such as carbon dioxide, hydrogen sulfide and other gases. Diffuser tubes are used to direct the air upwardly of a chamber defined by baffles. Recirculation is accomplished by the baffle arrangement providing an overflow below the liquid level which returns to the bottom of the chamber.

U.S. Pat. No. 3,605,850 discloses apparatus for the removal of relatively non-volatile contaminants from a thermally unstable organic chemical liquid. Stripping steam is introduced into the apparatus to remove the sulfolane as vaporized in a heat exchanger. The liquid portion of the mixture overflows the baffle and cascades downwardly in the space defined between the baffle and apparatus exterior walls to the liquid level below the baffle upper edge.

SUMMARY OF THE INVENTION

According to this invention, a single or multi-stage airlift reactor is used to separate a volatile component from aqueous solutions by gas stripping. Optionally, an organic solvent may be used to enhance the efficiency of stripping the desired volatile component from the solution. Various types of stripping gases may be used depending upon the conditions in the reactor and the miscibility of the desired volatile component to be recovered.

A process for removing a volatile component from a liquid solution, according to an aspect of the invention, comprises passing a stripping gas through the liquid solution. The liquid solution is contained in an upright vessel. An upright tube is provided in the vessel. The tube has an open bottom and an open top. A liquid level is maintained above the tube open top and below an outlet in an upper region of the vessel. The stripping gas is introduced into the tube open bottom, whereby the stripping gas flows upwardly of the tube. The upward flow of stripping gas induces circulation of the liquid solution upwardly of the tube out of the tube open top and dowhwardly of the vessel and returning to the tube open bottom. The gas stripping stream passes upwardly through the tube removing volatile components from the liquid solution to become thereby enriched with the volatile component. The enriched gas stripping stream exits from the tube open top and emerges from the liquid level into the upper vessel region for collecting the enriched stripping gas. The enriched stripping gas stream is passed out through a gas outlet in the vessel upper region. The volatile component is removed from the stripping gas.

According to another aspect of the invention, the process is particularly adapted for use in removing volatile metabolites produced during the culture on a continuous basis of microorganisms. To facilitate continuous culture of the microorganism, nutrients are introduced to the vessel and solids are removed from the liquid to control microorganism population in the liquid during continuous culture. The produced metabolites in the form of volatile components are continuously removed by the gas stripping stream.

According to another aspect of the invention, an apparatus for removing the volatile component from a liquid solution comprises an upright vessel for containing the liquid solution. Means forms an upright tube in the vessel having an open bottom and an open top. Means maintains a liquid level above the tube means. Means introduces a stripping gas into the open bottom of the tube means whereby the stripping gas flows upwardly of the tube. Means is provided above the tube for collecting stripping gas emerging from the liquid. The stripping gas is enriched in the volatile component removed from the liquid. Means transfers the enriched collected gas from the stripping gas collector to means for removing the volatile component from the stripping gas. Optionally, means may be provided for recirculating the stripping gas which is free of the volatile component after emerging from the means for removing the volatile component from the stripping gas.

According to a preferred aspect of the invention, the stripping gases, which pass through the reactor and provide for the necessary agitation of the culture within the reactor, may be varied during the fermentation phase to concur with the aerobic and anaerobic requirements of the microorganisms.

BRIEF DESCRIPTION OF THE DRAWINGS

Preferred embodiments of the invention are shown in the drawings, wherein.

DESCRIPTION OF THE PREFERRED EMBODIMENTS OF THE INVENTION

Figure 1:
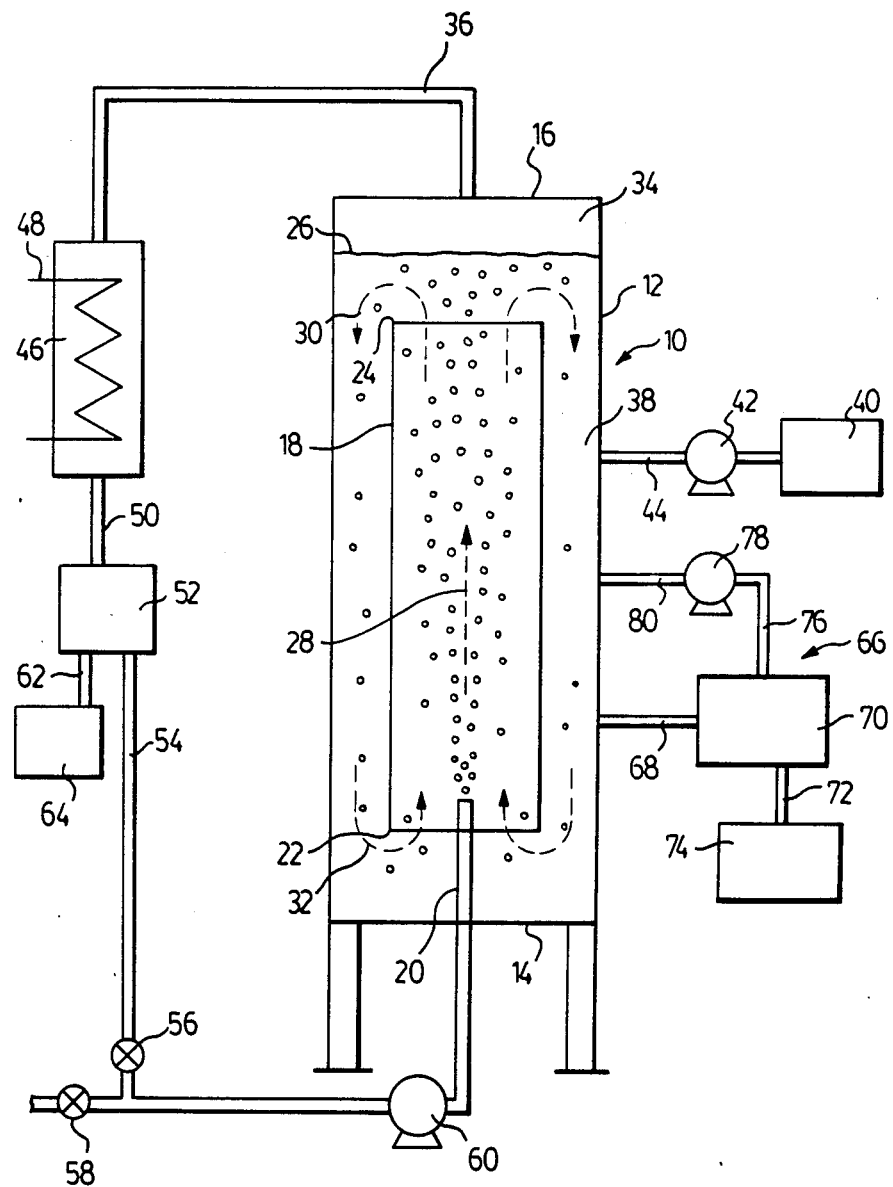
FIG. 1 is a schematic of an apparatus within which the process according to this invention is practised.

The apparatus according to an aspect of this invention is shown in FIG. 1. The apparatus comprises a reactor 10 having an outer vessel 12 with a closed bottom 14 and closed top 16. Supported within the vessel 12 is a shorter inner tube 18 which is located above the bottom 14. A stripping gas inlet conduit 20 extends upwardly beyond the bottom and to within the lower portion 22 of the tube 18. The upper portion 24 of the tube 18 is below the liquid level 26 as maintained within the reactor 10.

The selected stripping gas is introduced via conduit 20 into the tube 18 and bubbles upwardly in the direction of arrow 28. This causes a circulation of the solution in the direction of arrows 30 and 32 so that the liquid travels upwardly through the tube 18 and downwardly of the space 38. The tube 18 functions as a baffle to provide for the cyclic liquid flow pattern within the reactor vessel. Voidage in the liquid due to expansion of gas and the upward movement of the gas bubbles coupled by frictional forces to the liquid causes a circular pattern of flow which is upwardly of the central tube and down the annular space. Gas is also recycled in the liquid. This increases the gas residence time at high gas flow rates. It is appreciated that other baffle arrangements may be provided which define a tube having an open bottom and an open top and which may have configurations different than that shown in FIG. 1. The volatile components in the aqueous solution are collected in space 34 defined above the liquid level and pass outwardly through the top 16 via conduit 36. The collected vapors flow to a condensor to remove the stripped volatile components and any associated water. The gas, as purified in the condensor, may be returned to the gas inlet for recirculation.

The tube 18 may preferably be circular as located within a cylindrical vessel 12 to provide the annular space 38 between the tube and the wall of vessel 12.

Various arrangements may be provided to control and regulate the temperature of the liquids within the reactor vessel. The inner tube 18 may be double walled to provide for passage of heat transfer fluids circulating between the double walls of the draft tube. Furthermore about the perimeter of the vessel, temperature control elements may be provided in the form of a blanket in which cooling and heating mediums may flow.

The reactor, as discussed with respect to FIG. 1, may be used as a single-stage or in a multi-stage arrangement. The reactor, as used in this situation, need not include the peripheral condensor, liquid and solid separators and related pumping and tubing, such items being particularly suited for adapting the reactor to fermentation reactions. Envisaging the reactor 10 without the peripheral items, in a multi-stage arrangement the gas and vapor recovered from the upper portion 34 of the first reactor would be fed into the gas inlet of the next reactor. By this series arrangement for the reactor, the volatile component/water azeotrope is realized at a point along the series.

In a batch reactor operation, the solutions in either the single or series stages are stripped of the volatile component until concentrations are sufficiently low to dispose of the remaining aqueous phase in the reactors. Periodically the reactor can be replenished with concentrated solutions.

With the apparatus of this invention, high gas/liquid interfacial area is provided to make the reactor ideal for selective stripping of volatile components from the aqueous solution.

It has been found by controlled operation of this apparatus that the specific volatile component uptake in the stripping gas can be predicted based on the concentration of the volatile component in the liquid. The expression derived to calculate the specific volatile component uptake with varying concentration of that component in a liquid is as follows:

$$\sigma = \frac{K M_{av} \Sigma fi}{M_g (P - \Sigma fi)} \quad (I)$$

wherein
$\sigma$ is specific volatile uptake;
K is density for gas used;
$M_{av}$ is the "averaged" molecular weight, i.e.
$M_{av} = \Sigma x_j MW_j$, where $x_j$ and $MW_j$ are the mole fraction and molecular weight of the component i of the mixture respectively;
$\Sigma fi$ is the sum of the fugacities of the components where fi, the fugacity of the i-th component is calculated from $fi = x_j \sigma_j Pj°$ where $x_j$ is the mole fraction of the i-th component in the liquid $\sigma_j$ is the activity coefficient of the i-th component obtained independently, and $Pi°$ is the vapor pressure of the pure component i at the same conditions of temperature and pressure;
$M_g$ is the molecular weight of the stripping gas and P is the total system pressure.

When using moist air as the stripping gas, the constant K is 1.4 grams/liter. The volatilization rate is expressed in accordance with the formula:

$$r = f \sigma, \quad (II)$$

wherein r is the volatilization rate in terms of amount of material stripped per unit of time and f is the gas flow rate.

This arrangement is particularly useful in many areas including fermentation reactions, because the introduction of the gas provides the necessary agitation and circulation of the biomass within the reactor without necessitating any use of mechanical agitation. In addition, the reactor may be operated at the desired temperature for the fermentation broth without killing the microorganisms and not requiring the use of heat or the like for distilling the volatile component from the solutions.

Other advantages include the aspect that the fermenter and purifier system are embodied in the same vessel. Fermentation can occur at temperatures in the range of 40° to 60° C. to avoid as mentioned killing the microorganisms. The volatile component produced, for example depending on the type of fermentation, may be one of the group of ethanol, butanol, acetone, is removed in the stripping gas stream. Volatization of the components within the reactor allows enrichment of the stripping gas streams by virtue of the phase transition from liquid to vapor in the reactor. The volume reduction in the reactor, due to the removal of the volatiles, is compensated for by the addition of microorganism feedstock solution to maintain the continuous culture and thereby obviate the need to regrow the culture in repeated batch fermentations. Because the stripping gas contains only volatiles, the stillage produced from further enrichment of the volatiles will contain no slops or byproducts as is the case with standard batch fermentations of alcohols and the like. Stillage production is reduced to a fraction of that associated with conventional batch fermenter and distillation operations. The process, according to this invention, is particularly adapted to remove low concentrations of the volatile metabolite from the fermentation broth. In systems for producing ethanol, the process and apparatus can remove ethanol from the liquid at concentrations by weight in the range of 0.5% to 3%. Similarly with butanol manufacture, liquid concentrations of about 1% by weight can be treated.

Returning to FIG. 1, the apparatus 10 is adapted by the peripheral components to provide for a continuous culture fermentation reaction. According to an embodiment of the invention, a culture of a selected microorganism, for example *Saccharomyces cerevisiae* ATCC 4126 and 4132 or *Clostridium acetobutylicum* is grown in the apparatus which, in the case of yeast, is initially under aerobic conditions. In this instance, some or all of the sparging gas purged through the system is sterile air or oxygen. This initiates the vigorous growth phase of the yeast and, as fermentation begins, the oxygen is gradually replaced by carbon dioxide as the normal metabolic processes of the yeast proceed. Anaerobic microbes will simply be grown using pure carbon dioxide or nitrogen as the sparging gas until the organics generate their own anoxic gas. Nutrients for the initial growth are provided by an aqueous continuous feed containing a carbon source (sugar), sources of nitrogen and phosphorous and microbe nutrients (vitamins, trace elemens). As shown in FIG. 1, the feed may be contained in vessel 40 and pumped by pump 42 via conduit 44 into the annular zone 38 of the vessel to travel downwardly with the circulating medium. The dilution of the feed is controlled to balance the removal of liquid by volatization so that a constant volume is essentially maintained in the vessel.

The volatile metabolites, e.g. butanol or ethanol depending on the microorganism being cultured, are removed by uptake in the gas stream, where the gaseous phase separates from the liquid in region 34. The vapors leave the vessel 10 via conduit 36 and are passed into a condensor 46 with cooling water provided thereto in line 48. Energy recovery by vapor recompression in the condensation step may also be practiced. The gas from condensor 46 is recycled with residual volatiles, thus closing the system. This is achieved whereby the condensed volatiles leave the condensor 46 via line 50 and pass into a liquid/vapor separator 52. Any vapor remaining in the condensed stream is removed in the liquid/vapor separator 52 and travels via line 54 which, when valve 56 is open and valve 58 closed, the gases are recirculated via pump 58 upwardly of the reactor in the manner previously discussed. When the separated volatiles are not recirculated, the valve 56 is closed and the volatiles removed from line 54 in another manner. To supply the purging gas to the system, valve 58 is open and a suitable supply of gas is then passed to pump 60. The benefits, of course, in recycling the volatiles removed in separator 54 is in the reduction of the danger of infection, economy in the use of gas and elimination of loss of residual volatiles.

The liquid phase, as separated by separator 52, is transferred via line 62 to vessel 64 for collecting the desired condensed metabolites from the fermentation reaction.

A system of continuous or periodic spent cell removal is provided by system 66. The cells are removed from the liquor via line 68 and separated in a liquid solid separator 70, such as a centrifuge or filter. The solids are transferred via line 72 to a solid collector 74. The liquid separated in separator 70 may or may not be returned to the fermenter via line 76 using pump 78 which pumps the liquid into the reactor via line 80. As is appreciated in the art of fermentation, a stable cell population will be maintained by cell bleed rate and continuous or pulsed air injection.

The entire system may be placed under electronic control so that the stripping rate will match the rate of production of the metabolites, such as ethanol, butanol, acetone and the like. The important parameters, which are controllable, are the the gas flowrate, the temperature and the cell density. Typical operating concentrations for the ethanol fermentation by yeast are 2 weight percent ethanol in the broth and 10 weight percent in the condensate. These ranges will vary with the strain and tolerance of the microorganism used in the fermentation. In the cases of other types of fermentations and organisms, different product concentration levels will occur due to different terminal metabolite toxicity levels of the organism/product combination.

As can be appreciated by those skilled in the art, microorganisms may be fermented to produce a variety of volatile components, such as alcohols in particular methanol, ethanol and butanol and ketones such as acetone.

With standard fermentation reactions, the reactor may be operated in the temperature range of 30° to 70° C. and for the production of ethanol preferably in the range of 40° to 60° C.

Optionally an additional solvent may be added to the system to improve the stripping of the volatile component from the system and in particular in the stripping of ethanol from the solution. An additional solvent such as heptane may be used to improve the stripping. Heptane is removed with the other volatile components in the condensor and may be isolated and recirculated.

The gas supplied to this system is usually of large volume, low pressure thereby minimizing the energy requirements to pass the gas through the system. In maintaining the liquid level above the upper portion 24 of the tube, there is minimal shear or other physical agitation exerted on the system which could affect the productivity of the microorganisms. By this arrangement for the apparatus, excellent mixing of the liquid is provided which is particularly suited to fermentation reactions. The mixing is induced without mechanical shear which is the case in mechanical mixing. Mechanical mixing can harm the growth of the microorgansims which is undesirable.

In the multi-stage system, it is appreciated that in order to prevent extensive condensing requirements between the stages, lower reactor temperatures can be used as the ethanol concentration is increased. The off gas is used to sparge the subsequent stage.

EXAMPLE 1

Figure 2:
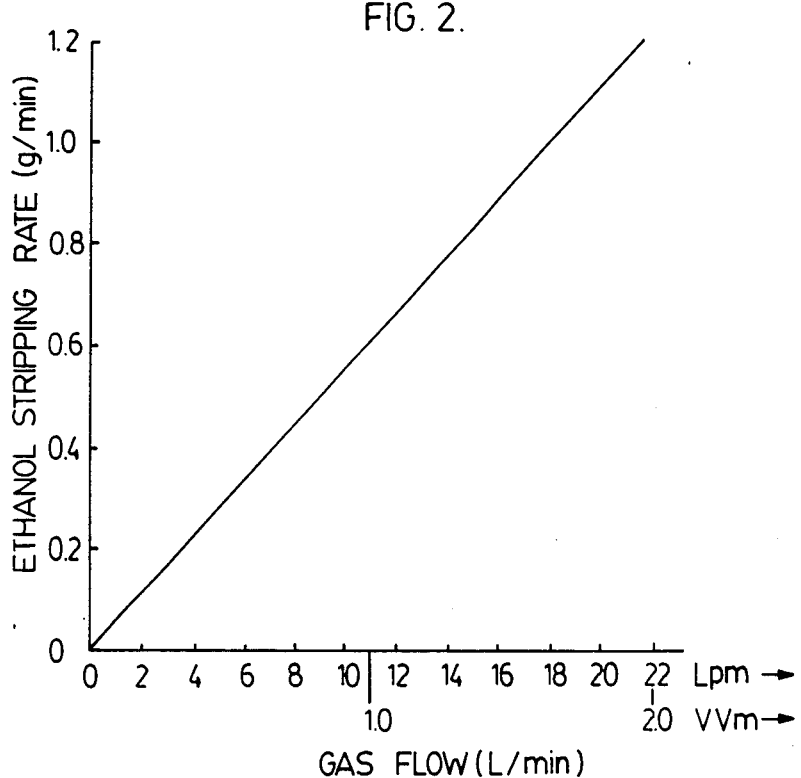
FIG. 2 is a graph demonstrating the ethanol stripping rate versus gas flow.
Figure 3:
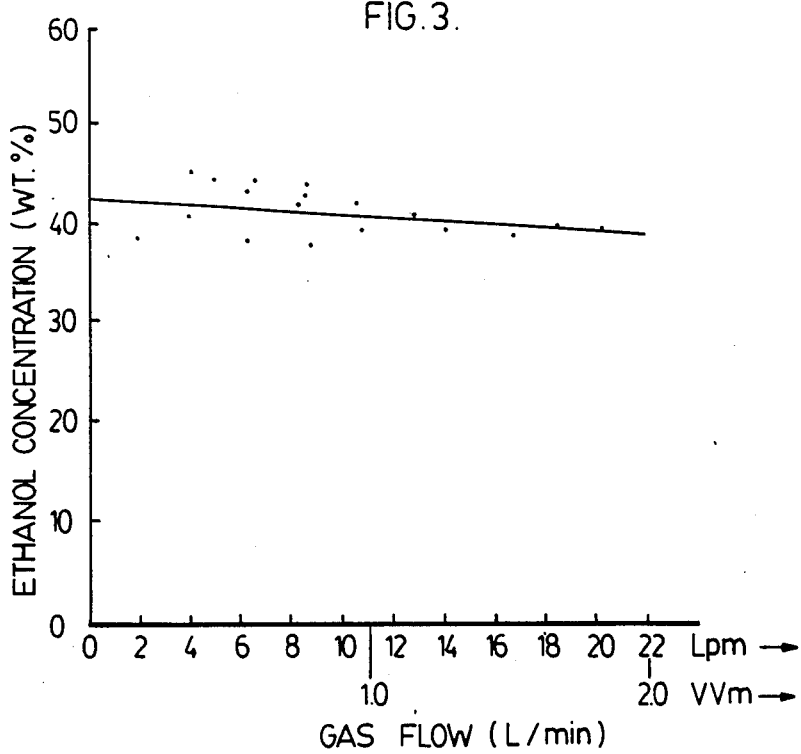
FIG. 3 is a graph demonstrating ethanol concentration in the vapor phase versus gas flow.

The apparatus of FIG. 1 was tested with a low concentration of ethanol in water and air as the stripping gas. The ethanol solution was premixed. The gas flow rate was varied to determine the effect of flow rate on the concentration of volatiles in the vapor phase. As shown in FIG. 2, the concentration of ethanol in the vapor phase and in the condensate was constant for gas flow rates in the range of 0.1 to 2.0 VVM (volume per minute). The rate of volatilizations and of condensate collection increased linearly with gas flow rate. It was found, as shown in FIG. 3, that the concentration in the vapor phase was constant with varying gas flow rate. In this apparatus, various sparging gases were tested to reveal that no changes were observed in the vapor composition of volatilization or condensation rates when the sparging gas was changed. Gases tested were air, helium, carbon dioxide and nitrogen. This result indicates a near ideal behavior in the gas phase of the volatile component under the operating conditions of low temperatures and pressures.

Figure 4:
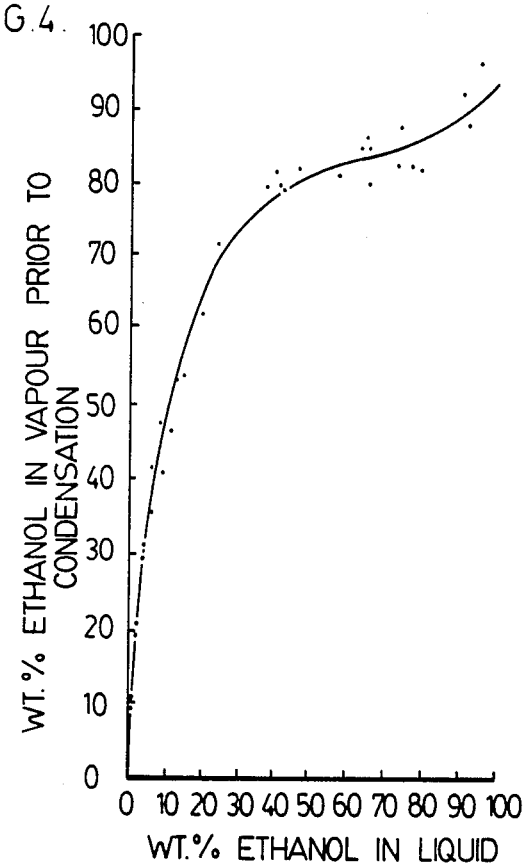
FIG. 4 is a graph illustrating a vapor liquid curve for ethanol in gaseous stripping stream versus ethanol in the liquid.

For the ethanol liquid system at 40° C., FIG. 4 illustrates the relationship of percent ethanol in vapor of the stripping gas in relation to the percent ethanol in liquid. This curve is surprisingly similar to the same curve for an ethanol water system at 100° C. This indicates that the ratio of ethanol to water in the vapor phase depends only on the concentration in the liquid phase of the ethanol over the temperature range of observation from 40° to 100° C.

Figure 5:
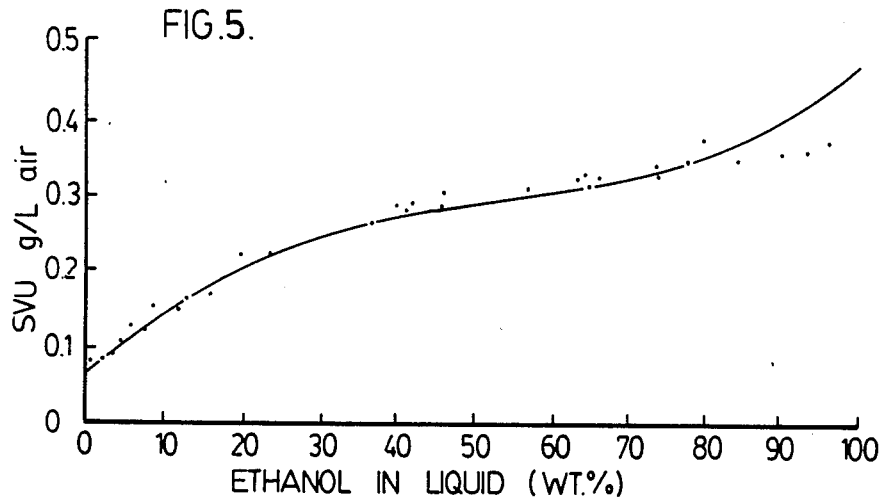
FIG. 5 is a graph illustrating the specific volatile uptake of ethanol as a function of ethanol concentration in the liquid at 40° C.

The result of FIG. 3 demonstrates that the ethanol concentration in the vapor phase is constant with respect to varying gas flow rate. As discussed, the constant $\sigma$ can be calculated in accordance with formula (I), where a plot of the specific volatile uptake $\sigma$ versus the concentration of ethanol in the liquid provides the result of FIG. 5. With this relationship, one can predict the concentration of ethanol in the gaseous phase knowing its concentration in the liquid within the reaction vessel.

It was found that the specific volatile uptake approximatley doubled for each 10° C. rise in temperature in the range of 40° to 60° C.

EXAMPLE 2

Fermentation was carried in the apparatus of FIG. 1 using two strains of Saccharomyces cerevisiae ATCC 4126 and 4132. Continuous culture took place in the reactor. Nutrient solutions were added from time to time within the vessel closure. The carbon source was glucose and the other mineral and trace requirements were provided by the chemicals $KH_2PO_4$, $H_2PO_4$, citric acids, sodium citrate, $MgSO_4$, $(NH_3)_2SO_4$ and yeast extract.

The growth of the culture was monitered by optical density at the early stages of the culture and by the ATP assay during the extended continuous run. This is the luciferin-luciferase enzyme assay where the bioluminescent response is a linear function of the ATP concentration of a quantitative extract of the cells.

Air was used as the stripping gas. Fermentation gas was subsequently recycled. The pH of the fermentation was maintain in the range of 5.5. It was allowed to decrease during the continuous extended run. Foaming was prevented by the addition of Dow-Corning H-10 antifoam agent. From time to time, cells were removed from the system to control population of cultured microorganisms within the reactor.

The growth and fermentability of both strains of microorganisms were not inhibited by vigorous gas sparging by the stripping gas of either air, nitrogen or carbon dioxide. The growth and fermentability of strain 4126 was similar at temperatures ranging from 25° to 40° C. under conditions of vigorous gas sparging.

Ethanol was removed by continuous gas stripping and spent cells were removed every 7 to 10 days by removal of a small portion of the broth. After removal of the cells, the superactive liquid was returned to the fermenter.

The yield and rate figures for the first one month segment of the continuous fermentation with continuous removal of ethanol is as follows:

| | |
|---|---|
| Duration of monitored segment of fermentation run | 799 hours |
| Volume condensate collected | 55.3 L |
| Concentration of pooled condensate | 77.3 g/L |
| Fermenter volume | 11 L |
| Yield | |
| Ethanol produced = | 4,274.69 g |
| Theoretical yield = | 4,624.55 g |
| Percentage yield = | 92.43% |
| Rate | |
| Ethanol production rate = | 5.418 g/h |
| Specific ethanol production rate = | 0.49 g/L-h |
| Hourly specific dilution rate | 0.006 h$^{-1}$ |
| (55.3/[11 × 789]) = | |

These results indicate that the specific rate of ethanol production is approximately one-third to one-half that of a batch fermentation. However when the down time for a batch fermentation including spoiled batches are considered, the continuous ethanol removal system, according to this invention, is considerably advantageous. Overall the apparatus and process, according to this invention, establishes a viable alternative to the standard batch fermentation approaches with subsequent distillation to produce concentrated forms of ethanol and other desired volatile metabolites.

Although various preferred embodiments of the invention have been described herein, it will be understood by those skilled in the art that variations may be made thereto without departing from the spirit of the invention or the scope of the appended claims.

The embodiments of the invention in which an exclusive property or privilege is claimed are defined as follows:

1. A process for continuous removal of low concentrations of a volatile metabolite from a continuous culture of microorganisms in a liquid media by passing a stripping gas through said liquid media, said process comprising containing said liquid media in an upright vessel, providing an upright tube in said vessel which has an open bottom and an open top, maintaining a liquid media level above said tube open top and below an outlet in an upper region of said vessel, culturing said microorganisms in said media on a continuous basis without cooling of said media thereby permitting culturing of said media at temperatures in excess of 30° C. to enhance production of said volatile metabolites, introducing in to said vessel nutrients to facilitate continuous culture of said microorgainisms, removing solids from said liquid media to control microorgainism population in said media during continuous culture, introducing said stripping gas into said tube open bottom whereby said stripping gas flows upwardly of said tube, said stripping gas being introduced at a gas flow rate substantially in excess of a normal gas flow rate used to induce circulation in said media, said upward flow of stripping gas also inducing circulation of said liquid media upwardly of said tube, out of said tube open top and downwardly of said vessel and returning to said tube open bottom, said gas stripping stream passing upwardly through said tube tube removing said volatile metabolite from said liquid media to become thereby enriched with said low concentration of volatile metabolite, said gas stripping stream enriched with said volatile metabolite exiting from said tube open top and emerging from said liquid media into said upper vessel region for collecting said enriched stripping gas, passing said enriched stripping gas out through a gas outlet in said vessel upper region and removing said volatile metabolite from said stripping gas.

2. A process of claim 1, wherein said stripping gas is recirculated to said vessel after said volatile component is removed.

3. A process of claim 1 or 2, wherein said volatile component is removed from said enriched stripping gas by cooling said enriched stripping gas to condense said volatile component and collect the condensate.

4. A process of claim 1, wherein said stripping gas is introduced into said lower region of said vessel beneath said tube in finely divided bubbles.

5. A process of claim 4, wherein said stripping gas is introduced through a gas diffuser.

6. A process of claim 1, wherein said tube is positioned centrally of said vessel and spaced from interior walls of said vessel to define a liquid downflow region between said tube and said vessel.

7. A process of claim 6, wherein said vessel is circular and said tube is circular to provide an annular liquid downflow space between said tube and vessel interior.

8. A process of claim 2, wherein a solvent is added to said liquid to enhance stripping of said volatile metabolite from said liquid by said stripping gas.

9. A process of claim 1, wherein said volatile component is a metabolite produced by culturing microorganisms in said liquid.

10. A process of claim 9, wherein said volatile metabolite produced is ethanol from culturing a yeast population of microorganisms.

11. A process of claim 10, wherein said microorganism is selected from the group consisting of *Saccharomyces cerevisiae*.

12. A process of claim 9, wherein said stripping gas is introduced in finely divided bubbles, said stripping gas containing oxygen during aerobic culturing of said microorganisms.

13. A process of claim 12, wherein said stripping gas is air.

14. A process of claim 12, wherein said stripping gas is nitrogen, helium or carbon dioxide during anaerobic culturing of said microorganisms.

15. A process of claim 1 wherein the rate of volatile component take up by stripping gas is predetermined in accordance with the formula:

$$\sigma = \frac{K M_{av} \Sigma fi}{M_g (P - \Sigma fi)}$$

wherein
$\sigma$ is specific volatile uptake;
K is density for gas used;
$M_{av}$ is the "averaged" molecular weight, i.e.
$M_{av} = \Sigma x_j MW_j$, where $x_j$ and $MW_j$ are the mole fraction and molecular weight of the component i of the mixture respectively;
$\Sigma fi$ is the sum of the fugacities of the components where fi, the fugacity of the i-th component is calculated from $fi = x_j \sigma_j Pj°$ where $x_j$ is the mole fraction of the i-th component in the liquid $\sigma_j$ is the activity coefficient of the i-th component obtained independently, and Pi° is the vapor pressure of the pure component i at the same conditions of temperature and pressure;
$M_g$ is the molecular weight of the stripping gas and P is the total system pressure.

16. A process of claim 15, wherein K is 1.4 for moist air.

* * * * *